(12) United States Patent
Wang

(10) Patent No.: US 11,712,500 B1
(45) Date of Patent: Aug. 1, 2023

(54) HANDS-FREE WEARABLE BREAST PUMP

(71) Applicant: Min Lv, Shenzhen (CN)

(72) Inventor: Kun Wang, Shenzhen (CN)

(*) Notice: Subject to any disclaimer, the term of this patent is extended or adjusted under 35 U.S.C. 154(b) by 0 days.

(21) Appl. No.: 17/972,878

(22) Filed: Oct. 25, 2022

(30) Foreign Application Priority Data

Jul. 27, 2022 (CN) .......................... 202210903391.2

(51) Int. Cl.
*A61M 1/06* (2006.01)
(52) U.S. Cl.
CPC ................................. *A61M 1/067* (2021.05)
(58) Field of Classification Search
CPC ........ A61M 1/06; A61M 1/062; A61M 1/064; A61M 1/066; A61M 1/068; A61M 1/0697; A61M 1/007; A61M 2210/1007; A61M 1/067; A61B 2018/00333; A61J 13/00
See application file for complete search history.

(56) References Cited

U.S. PATENT DOCUMENTS

| | | | |
|---|---|---|---|
| 11,554,199 B1* | 1/2023 | Chen ....................... | A61M 1/06 |
| 2018/0361040 A1* | 12/2018 | O'Toole ................. | G16H 40/63 |
| 2022/0111128 A1* | 4/2022 | Visconti ................. | A61M 1/062 |
| 2022/0249750 A1* | 8/2022 | Visconti ................. | A61M 1/064 |
| 2022/0265907 A1* | 8/2022 | Hwang ................... | A61M 1/067 |

\* cited by examiner

*Primary Examiner* — Emily L Schmidt
*Assistant Examiner* — William R Frehe

(57) ABSTRACT

The present invention discloses a hands-free wearable breast pump which includes: a main pump body, a milk reservoir, a tee piece, an airbag and a duckbill valve. The main pump body is provided with a mounting cavity having an opening in a front end surface of the main pump body; the tee piece includes a first port, a second port for mounting the airbag and a third port for mounting the duckbill valve; the airbag is mounted to the second port; the duckbill valve is mounted to the third port; the milk reservoir is mounted to the tee piece or the main pump body; the duckbill valve is in fluid communication with the milk reservoir; the main pump body has at least one pushing and positioning structure formed in the mounting cavity; the tee piece is detachably mounted in the mounting cavity and abuts against the at least one pushing and positioning structure; and the tee piece is pushed upward by the at least one pushing and positioning structure to press an open end of the airbag tightly against a side wall of the mounting cavity. The hands-free wearable breast pump has the advantages of excellent sealing performance and convenient disassembly and assembly.

8 Claims, 9 Drawing Sheets

HANDS-FREE WEARABLE BREAST PUMP

CROSS REFERENCE

This application claims priority benefit of Chinese Invention Application No. 202210903391.2, filed on Jul. 27, 2021, and the entire contents of which are incorporated herein by reference.

TECHNICAL FIELD

The present invention relates to the field of breast pumps, and in particular to a hands-free wearable breast pump.

BACKGROUND

Existing hands-free wearable breast pumps has gained widespread popularity in the market because they are convenient to use and can free hands of mothers. Such a breast pump typically includes a main pump body, a breast shield, a milk reservoir, a tee piece, an airbag, a duckbill valve, etc. During use, the breast shield is placed over a breast, milk is repeatedly sucked out by controlling expansion and contraction of the airbag, and the milk flows into the milk reservoir through the duckbill valve. However, the airbag of such a breast pump has poor sealing performance and thus is prone to leakage during use, which affects normal use. Moreover, such a breast pump includes many loose parts which have complex connection relationships, so it is difficult to reassemble quickly after disassembly.

Therefore, there is an urgent need for a hands-free wearable breast pump with excellent sealing performance to overcome the above defects.

SUMMARY

An objective of the present invention is to provide a hands-free wearable breast pump with excellent sealing performance.

In order to achieve the above objective, the present invention provides a hands-free wearable breast pump, including: a main pump body, a milk reservoir, a tee piece, an airbag and a duckbill valve. The main pump body is provided with a mounting cavity having an opening in a front end surface of the main pump body; the tee piece includes a first port, a second port for mounting the airbag and a third port for mounting the duckbill valve; the airbag is mounted to the second port; the duckbill valve is mounted to the third port; the milk reservoir is mounted to the tee piece or the main pump body; the duckbill valve is in fluid communication with the milk reservoir; the main pump body has at least one pushing and positioning structure formed in the mounting cavity; the tee piece is detachably mounted in the mounting cavity and abuts against the at least one pushing and positioning structure; and the tee piece is pushed upward by the at least one pushing and positioning structure to press an open end of the airbag tightly against a side wall of the mounting cavity.

As an improvement, the first port of the tee piece is integrally formed into a breast shield structure; and the breast shield structure penetrates through the front end surface of the main pump body.

As an improvement, a rear side of the tee piece is formed with a counter pushing and positioning structure; the counter pushing and positioning structure and the at least one pushing and positioning structure are arranged to abut against each other; a bottom surface of the counter pushing and positioning structure is a horizontally arranged flat structure; a top portion of the at least one pushing and positioning structure is a horizontal structure; and a front side surface of the at least one pushing and positioning structure is arranged obliquely.

As an improvement, the mounting cavity is surrounded by a rear side surface opposite the front end surface and left and right side surfaces; and the main pump body is provided with a plurality of the pushing and positioning structures protruding from the rear side surface and arranged side by side at intervals.

As an improvement, the main pump body is provided with two limiting structures protruding from the rear side surface and arranged at an interval with one on the left and the other on the right; the limiting structures are arranged above the at least one pushing and positioning structure; the two limiting structures and the at least one pushing and positioning structure define a positioning space; and the counter pushing and positioning structure is arranged in the positioning space.

As an improvement, the limiting structures are vertically extending tab structures; the two limiting structures are symmetrically arranged opposite each other with one on the left and the other on the right; the rear side of the tee piece is also formed with an auxiliary positioning structure; the auxiliary positioning structure is located above the counter pushing and positioning structure; the auxiliary positioning structure and the counter pushing and positioning structure are horizontally extending tab structures; the auxiliary positioning structure is arranged in the positioning space; and the rear side of the tee piece is formed with a connecting structure connecting the counter pushing and positioning structure and the auxiliary positioning structure.

As an improvement, the main pump body includes a press cover arranged at the top of the mounting cavity; the press cover has a support ring protruding towards the mounting cavity; the open end of the airbag is snap-fitted to the second port of the tee piece; the second port of the tee piece and the press cover compress the open end of the airbag together; the support ring extends into the airbag; the press cover and the airbag define a compressible air chamber of variable volume; and the press cover is provided with an air outlet and an air inlet in fluid communication with the compressible air chamber.

As an improvement, a connecting boss protrudes from a top portion of the milk reservoir, the connecting boss is provided with a channel in fluid communication with an inner cavity of the milk reservoir; the duckbill valve extends through the channel; the connecting boss includes a snap-fit structure; the main pump body includes a counter snap-fit structure; and the milk reservoir is detachably mounted to the main pump body by snap fit of the snap-fit structure and the counter snap-fit structure.

As an improvement, the airbag includes an annular structure and a deformation structure protruding downward and connected to the annular structure; the deformation structure is centered in the annular structure; and a thin layer structure is arranged at a joint of the annular structure and the deformation structure and/or at the center of the deformation structure.

As an improvement, an end part of the first port of the tee piece is provided with a hook-shaped snap structure; the open end of the airbag is formed with a flanging structure arranged outward; and the flanging structure is snap-fitted to the hook-shaped snap structure.

Compared with the related art, because the tee piece is detachable, the tee piece can be removed for cleaning and disinfection after use. After the tee piece is mounted in place, the tee piece is pushed upward by the pushing and positioning structure, the pushing and positioning structure exerts a force on the tee piece, and the second port of the tee piece presses against the side wall of the mounting cavity, so that the second port presses the open end of the airbag to the side wall of the mounting cavity, and the open end of the airbag and the side wall of the mounting cavity are closely attached to each other. The sealing effect of the airbag is good, the sealing performance of the breast pump is superior, air leakage is prevented, and normal use of the breast pump is guaranteed.

DETAILED DESCRIPTION

Figure 1:
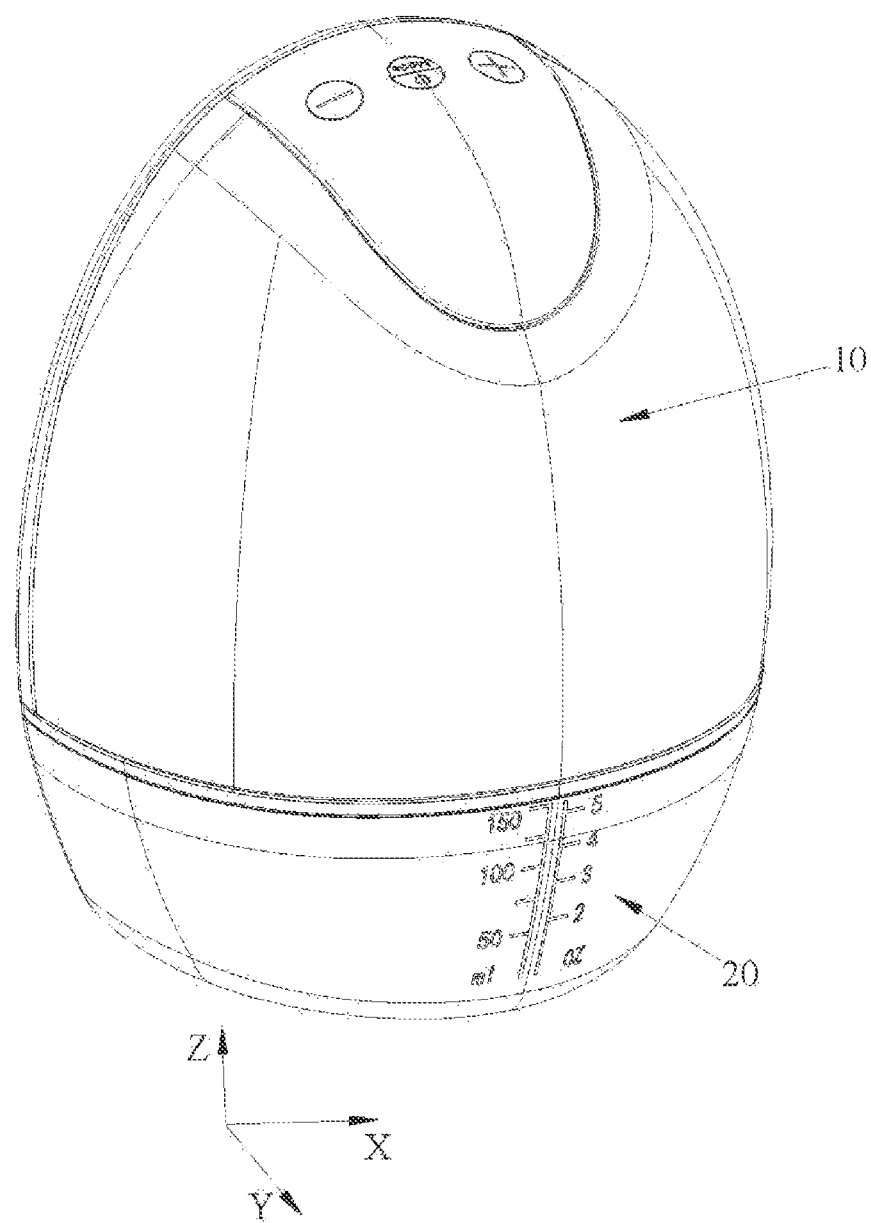
FIG. 1 is a perspective view of a breast pump.

In order to explain in detail the technical contents and structural features of the present invention, further description is given below in conjunction with the embodiments and with the accompanying drawings.

As shown in FIGS. 1-9 and FIG. 11, a hands-free wearable breast pump 100 of the present invention includes: a main pump body 10, a milk reservoir 20, a tee piece 30, an airbag 40 and a duckbill valve 50. Specifically, "hands-free wearable" means that a mother who is ready to pump breast milk can put the breast pump 100 into an underwear after wearing the underwear (or a chest strap), and the breast pump 100 is positioned and supported by the underwear, so it is not necessary to hold the pump by hand during use, thereby freeing the mother's hands.

The main pump body 10 is provided with a mounting cavity 11 having an opening in a front end surface of the main pump body. The tee piece 30 includes a first port D1, a second port D2 for mounting the airbag 40 and a third port D3 for mourning the duckbill valve 50. The airbag 40 is mounted to the second port D2, and the duckbill valve 50 is mounted at the third port D3. In this embodiment, the milk reservoir 20 is mounted to the main pump body 10, and of course, the milk reservoir 20 may be mounted to the tee piece 30 according to actual needs. The duckbill valve 50 is in fluid communication with the milk reservoir 20. The main pump body 10 has at least one pushing and positioning structure 12 formed in the mounting cavity 11. The tee piece 30 is detachably mounted in the mounting cavity 11 and abuts against the at least one pushing and positioning structure 12. The tee piece 30 is pushed upward by the at least one pushing and positioning structure 12 to press an open end of the airbag 40 tightly against a side wall of the mounting cavity 11.

Figure 3:
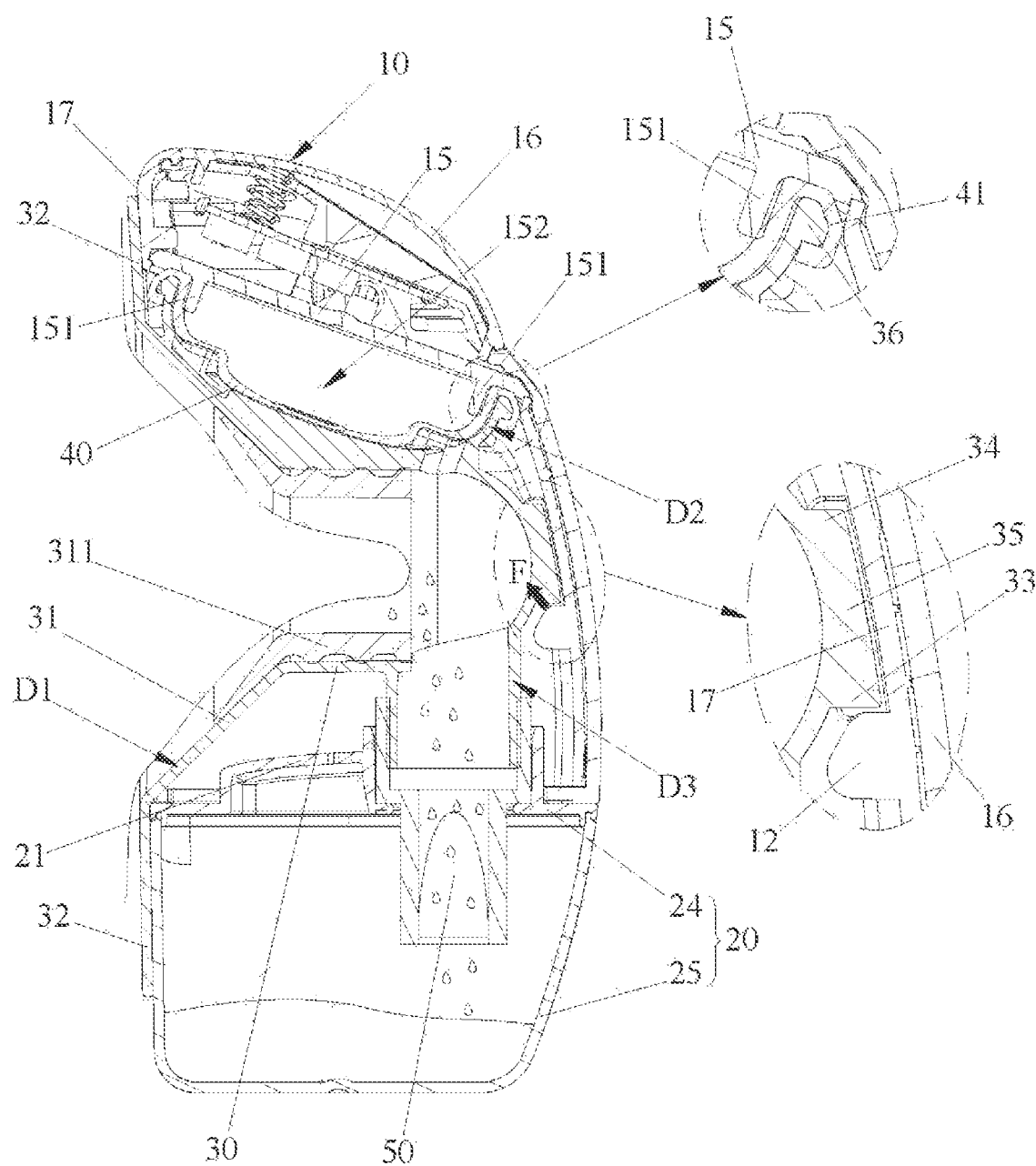
FIG. 3 is a cross-sectional view of the breast pump during breast pumping.
Figure 4:
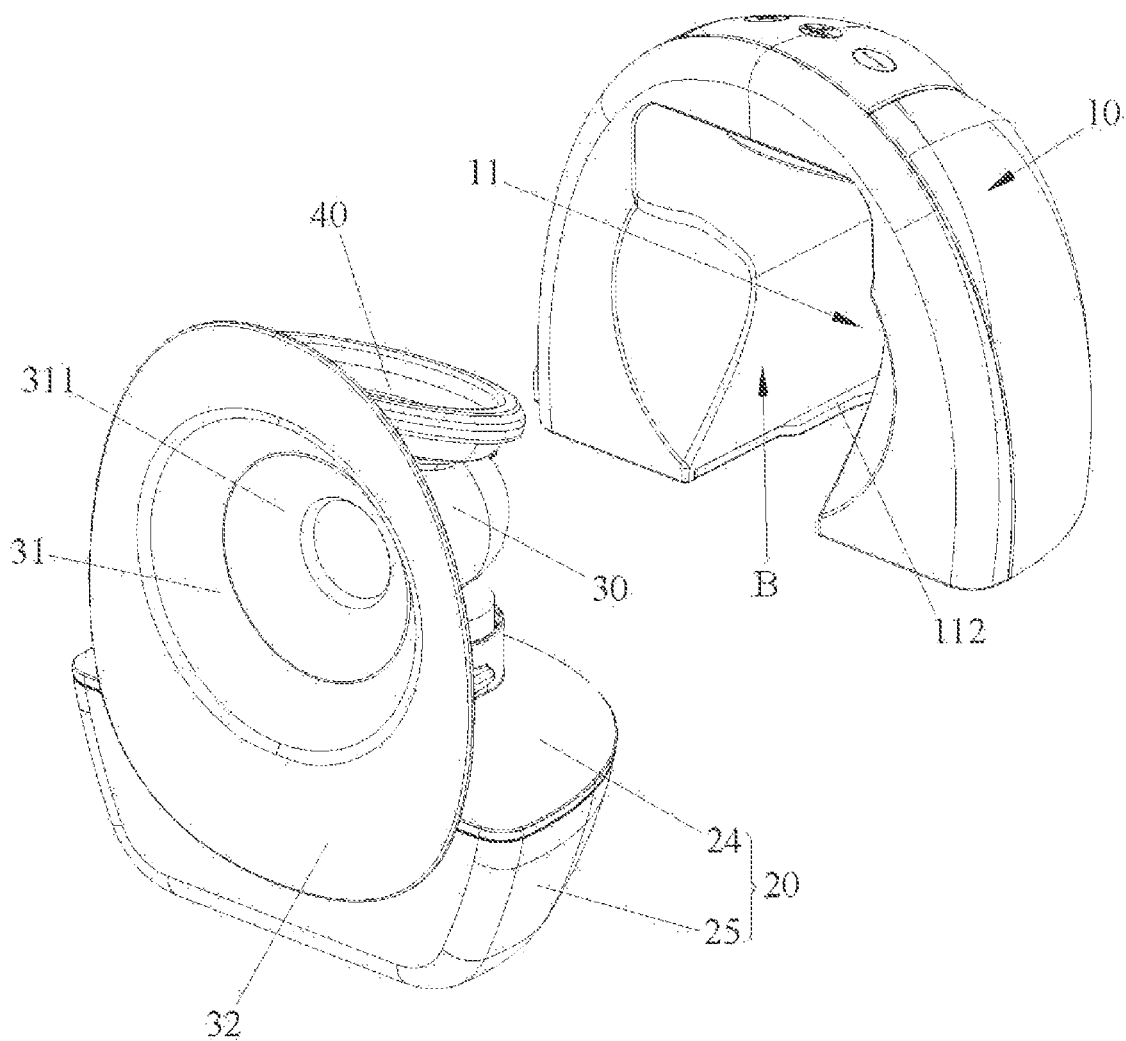
FIG. 4 is a perspective view of the breast pump after removal of a tee piece and a milk reservoir from a main pump body.
Figure 5:
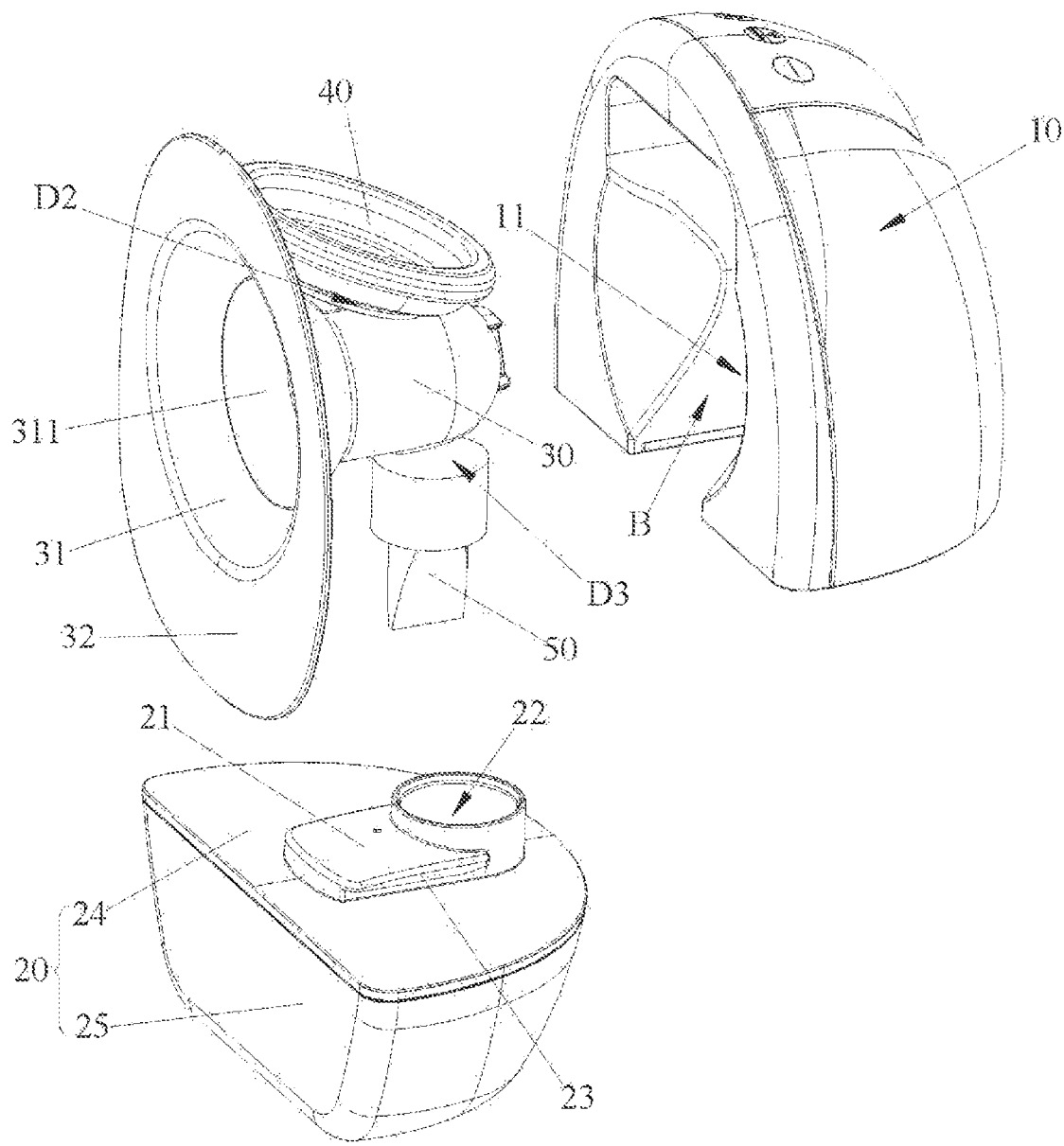
FIG. 5 is a perspective view of the milk reservoir in FIG. 4 after being further separated from the tee piece.
Figure 6:
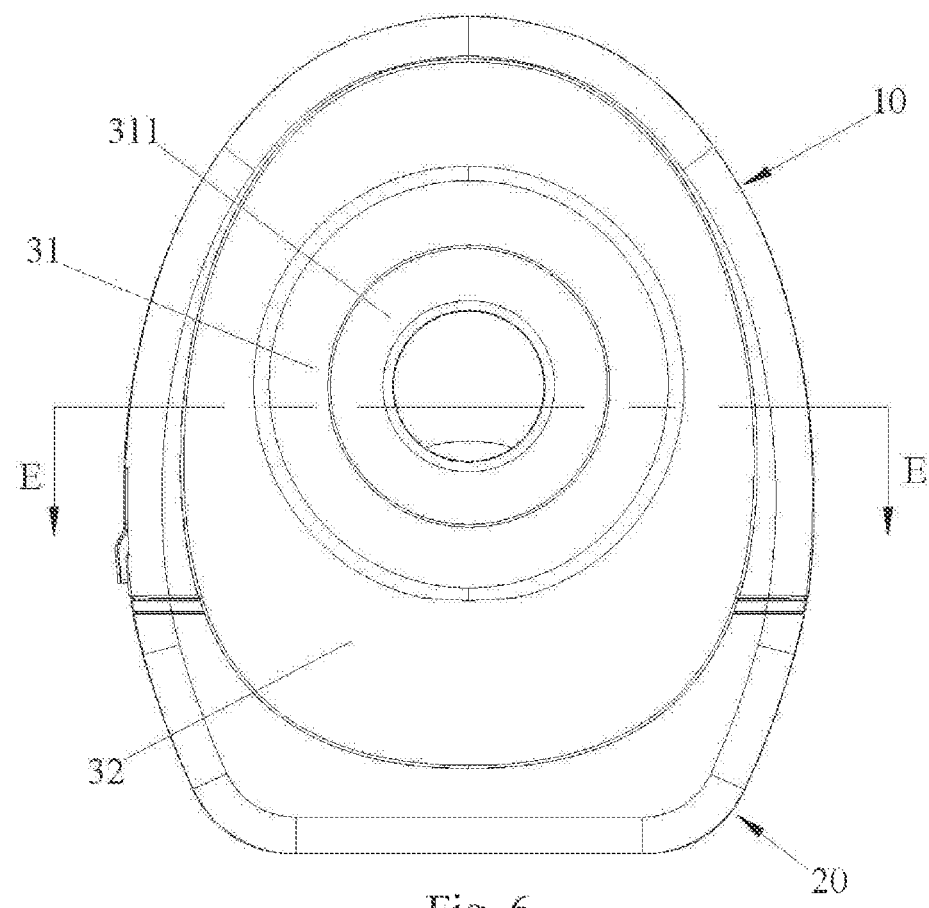
FIG. 6 is a front view of the breast pump.
Figure 7:
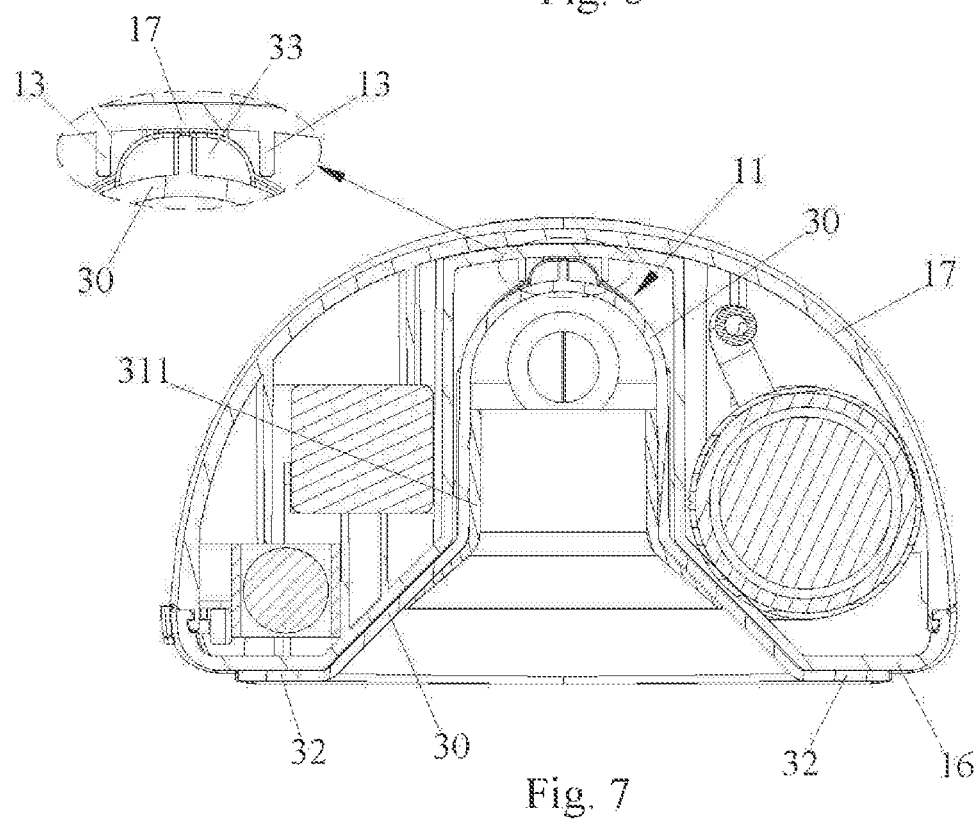
FIG. 7 is a cross-sectional view taken along line E-E of FIG. 6.
Figure 8:
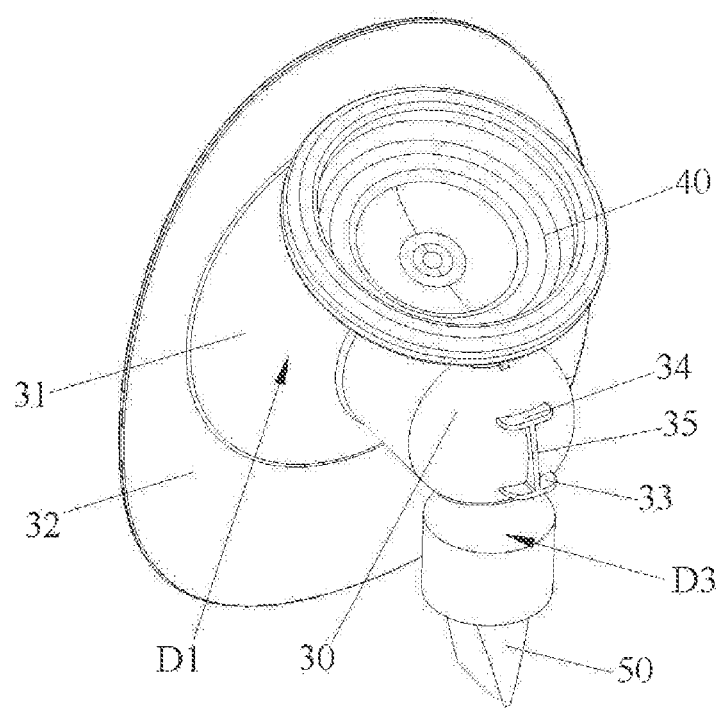
FIG. 8 is a perspective view of the breast pump after hiding the main pump body and the milk reservoir.
Figure 9:
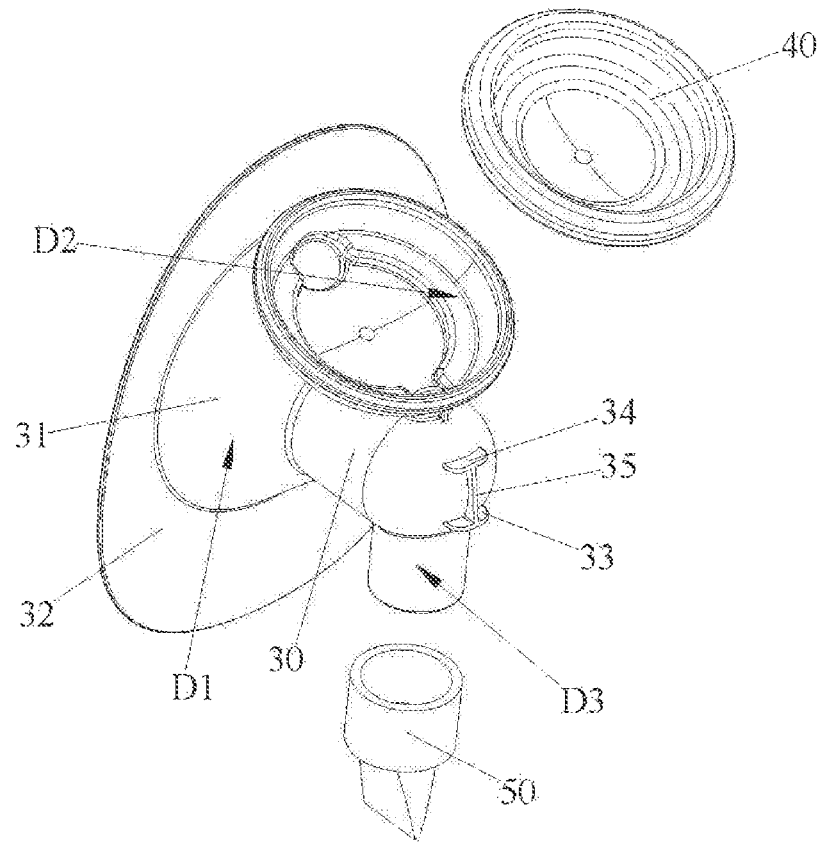
FIG. 9 is a perspective view of an airbag and a duckbill valve in FIG. 8 separated from the tee piece.

Because the tee piece 30 is detachable, the tee piece 30 can be removed for cleaning and disinfection after use. As shown in FIG. 3, after the tee piece 30 is mounted in place, the tee piece 30 is pushed upward by the pushing and positioning structure 12, the pushing and positioning structure 12 exerts a force on the tee piece 30, and the second port D2 of the tee piece 30 presses against the side wall of the mounting cavity 11, so that the second port D2 presses the open end of the airbag 40 to the side wall of the mounting cavity 11, and the open end of the airbag 40 and the side wall of the mounting cavity 11 are closely attached to each other. The sealing effect of the airbag 40 is good, the sealing performance of the breast pump 100 is superior, and normal use of the breast pump 100 is guaranteed.

As an improvement, the first port D1 of the tee piece 30 is integrally formed into a breast shield structure 31, and the breast shield structure 31 penetrates through the front end surface of the main pump body 10. The tee piece 30 is integrally formed into the breast shield structure 31, which can reduce the number of parts, so that a more stable structure and more convenient disassembly and assembly are enabled. Of course, according to actual needs, the breast shield structure 31 may also be manufactured separately, in which case the breast shield structure 31 can be mounted to the first port D1 of the tee piece 30.

An edge portion 32 of the breast shield structure 31 is bent and extends in a circumferential direction, and the edge portion 32 is attached to the front end surface of the main pump body 10, so that the structure is more compact. When the breast shield structure 31 is placed over a breast, the edge portion 32 is attached to the skin near the breast, so that the breast is better wrapped up, and imprints on the breast can be avoided, thereby improving user comfort.

In order to further improve the user comfort, a nipple sleeve 311 is detachably mounted in the breast shield structure 31. During use, a nipple is put into the nipple sleeve 311, and the nipple is fixed in place to avoid excessive wobbling. As an improvement, the nipple sleeve 311 adopts a silica gel structure, which is skin-friendly and soft. Due to individual differences, the size of nipples may vary from person to person, and the breast shield structure 31 can be mounted with nipple sleeves 311 in multiple sizes. In this embodiment, the nipple sleeves 311 come in three different sizes for people to choose, which is not limited thereto.

As shown in FIGS. 3-9 and FIG. 11, the rear side of the tee piece 30 is formed with a counter pushing and positioning structure 33. The counter pushing and positioning structure 33 and the pushing and positioning structure 12 are arranged to abut against each other. The bottom surface of the counter pushing and positioning structure 33 is a horizontally arranged flat structure, and the top of the pushing and positioning structure 12 is a horizontal structure, so that the pushing and positioning structure 12 can stably support the tee piece 30 and realize stable bias against the tee piece 30. A front side surface of the pushing and positioning structure 12 is arranged obliquely. Specifically, the front side surface of the pushing and positioning structure 12 is arranged obliquely from front to rear. When the tee piece 30 is mounted, the counter pushing and positioning structure 33 can slide along the front side surface of the pushing and positioning structure 12 to the top of the pushing and positioning structure 12, so that the tee piece 30 can be quickly mounted in place. When the tee piece 30 is removed, the tee piece 30 can also be quickly removed along the front side surface of the pushing and positioning structure 12. Further, the mounting cavity 11 is defined by a rear side surface A opposite the front end surface and left and right side surfaces B and C, and the main pump body 10 is provided with a plurality of pushing and positioning structures 12 protruding from the rear side surface A and arranged side by side at intervals. The plurality of pushing and positioning structures 12 can more stably support the counter pushing and positioning structure 33, and the force applied to the tee piece 30 is more balanced, so that all portions of the open end of the airbag 40 are effectively pressed to the inner side wall of the main pump body 10. The tee piece 30 mounted in the mounting cavity 11 will not be displaced easily because of limiting of the rear side surface A and the left and right side surfaces B and C, thus improving structural stability.

As shown in FIGS. 3-9 and FIG. 11, the main pump body 10 is provided with two limiting structures 13 protruding from the rear side surface A and arranged at an interval with one on the left and the other on the right, the limiting structures 13 are arranged above the at least one pushing and positioning structure 12, the two limiting structures 13 and the pushing and positioning structure 12 define a positioning space 14, and the counter pushing and positioning structure 33 is arranged in the positioning space 14. Thus, left and right sides of the counter pushing and positioning structure 33 are limited by the limiting structures 13, so that the tee piece 30 is prevented from moving horizontally, the counter pushing and positioning structure 33 is pushed by the pushing and positioning structure 12 and cannot move downward, and the tee piece 30 is prevented from moving up while pressing the open end of the airbag 40 to the side wall of the mounting cavity 11, so that the tee piece 30 is limited from upper, lower, left and right aspects, and the structural stability of the breast pump 100 is improved.

Specifically, the limiting structures 13 are vertically extending tab structures; the two limiting structures 13 are symmetrically arranged opposite each other with one on the left and the other on the right; the rear side of the tee piece 30 is also formed with an auxiliary positioning structure 34; the auxiliary positioning structure 34 is located above the counter pushing and positioning structure 33; the auxiliary positioning structure 34 is arranged in the positioning space 14; and the rear side of the tee piece 30 is formed with a connecting structure 35 connecting the counter pushing and positioning structure 33 and the auxiliary positioning structure 34. After the tee piece 30 is mounted in place, both the counter pushing and positioning structure 33 and the auxiliary positioning structure 34 comes into the positioning space 14, and the auxiliary positioning structure 34 is also limited by the two limiting structures 13 on the left and right sides, so that the tee piece 30 is horizontally retained in place firmly as both an upper part and a lower part of the tee piece 30 are limited on the left and right sides. The connecting structure 35 connects the counter pushing and positioning structure 33 and the auxiliary positioning structure 34, so that the auxiliary positioning structure 34 is better supported by the counter pushing and positioning structure 33, and the counter pushing and positioning structure 33 and the auxiliary positioning structure 34 are not prone to breakage.

As shown in FIGS. 3, 8, 9, 11 and 12, the main pump body 10 includes a press cover 15 arranged at the top of the mounting cavity 11, and the press cover 15 has a support ring 151 protruding towards the mounting cavity 11. The open end of the airbag 40 is snap-fitted the second port D2 of the tee piece 30; the second port D2 of the tee piece 30 and the press cover 15 compress the open end of the airbag 40 together, so that an opening edge of the airbag 40 is compressed tightly without air leakage. The support ring 151 extends into the airbag 40 to provide support for the airbag 40 and prevent the airbag 40 from collapsing due to excessive contraction. The press cover 15 and the airbag 40 define a compressible air chamber 152 of variable volume; and the press cover 15 is provided with an air outlet 153 and an air inlet 154 in fluid communication with the compressible air chamber 152.

During use, after air in the compressible air chamber 152 is pumped out, the airbag 40 contracts, a negative pressure environment is formed in the tee piece 30, and the negative pressure acts on the breast to suck the milk out of the breast. After the compressible air chamber 152 is inflated, the airbag 40 is restored to its original shape. This process is repeated again and again such that the milk can be continuously sucked out. The milk can flow through the duckbill valve 50 into the milk reservoir 20 for storage.

Figure 12:
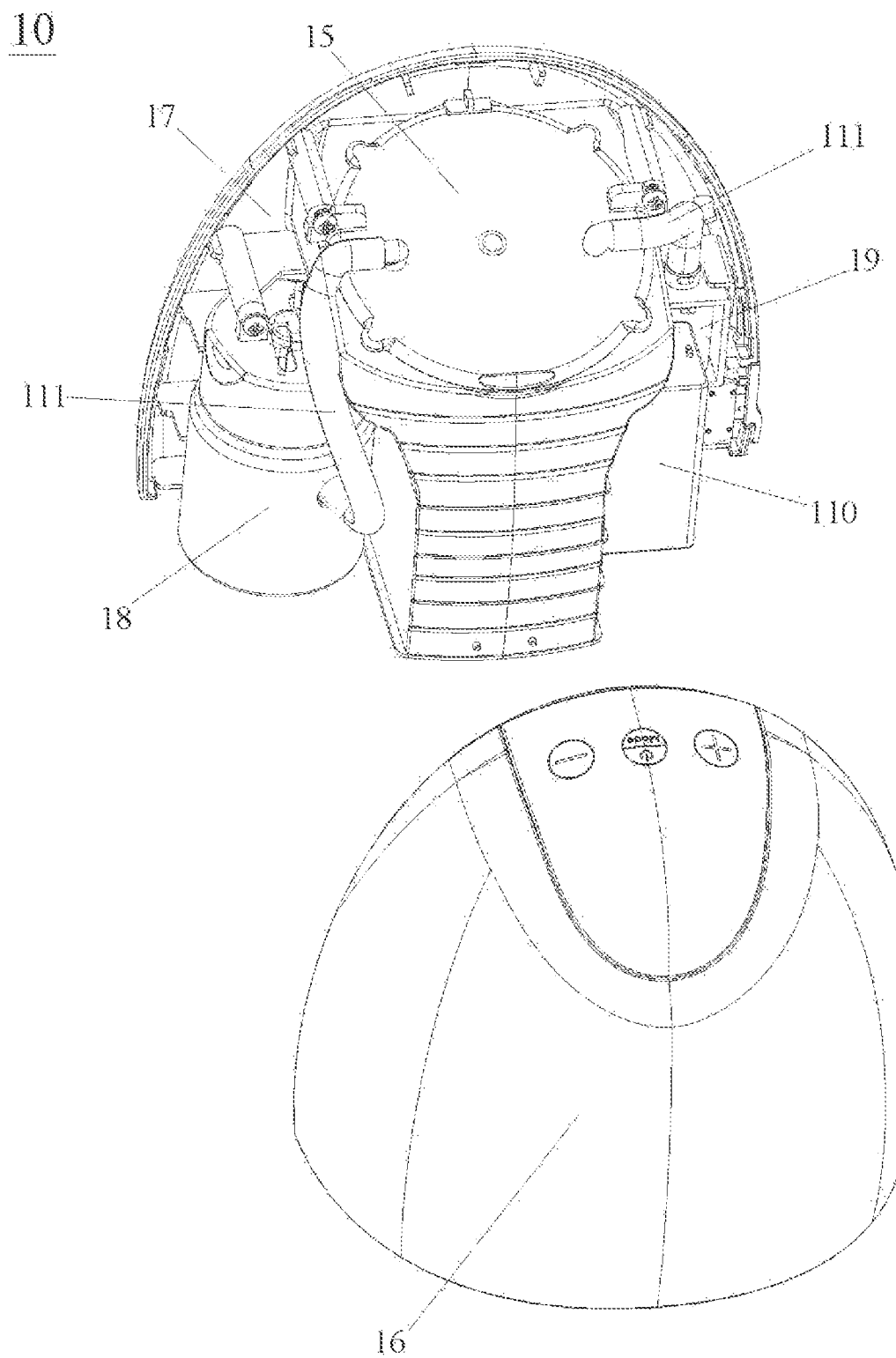
FIG. 12 is an exploded view of the main pump body.

As shown in FIG. 12, the breast pump 100 is "computer mouse-shaped", but is not limited thereto. The front end surface of the main pump body 10 is a flat surface, so that the surface can fit conformably against the skin of a user. In particular, the main pump body 10 includes a first housing 16, a second housing 17, an air pump 18, a solenoid valve 19 and a battery 110. The first housing 16 and the second housing 17 define an accommodation cavity (not indicated) in which the air pump 18, the solenoid valve 19 and the battery 110 are accommodated. Specifically, the air pump 18 is in fluid communication with the air outlet 153 via an air pipe 111, the solenoid valve 19 is in fluid communication with the air inlet 154 via another air pipe 111, and the battery 110 is electrically connected to the air pump 18 and the solenoid valve 19, respectively. The battery 110 supplies power to the air pump 18 and the solenoid valve 19, and the battery 110 is preferably a rechargeable battery, but is not limited thereto.

During use, the air pump 18 pumps air out of the compressible air chamber 152 to suck out milk, and then the solenoid valve 19 is opened, so that the compressible air chamber 152 comes into fluid communication with the atmosphere, and air flows into the compressible air chamber 152 to restore the airbag 40 to its original shape. The first housing 16 is also provided with a start function mode control button and strength/frequency control buttons to facilitate control of the breast pump 100.

As shown in FIGS. 3-5 and FIG. 11, the duckbill valve 50 is detachably mounted to the third port D3 of the tee piece 30. A connecting boss 21 protrudes from a top portion of the milk reservoir 20; the connecting boss 21 is provided with a channel 22 in fluid communication with an inner cavity of the milk reservoir 20; the duckbill valve 50 extends through the channel 22; the connecting boss 21 includes a snap-fit structure 23; the main pump body 10 includes a counter snap-fit structure 112; and the milk reservoir 20 is detachably mounted to the main pump body 10 by snap fit of the snap-fit structure 23 and the counter snap-fit structure 112.

As an improvement, the snap-fit structure 23 and the counter snap-fit structure 112 are snapped to each other vertically, the snap-fit structure 23 extends in front and rear directions, and the counter snap-fit structure 112 is a ledge structure. After use of the breast pump 100, the milk reservoir 20, the duckbill valve 50, the tee piece 30 and the airbag 40 can be removed all together, and then the main pump body 10 can be separated from all the other parts. Then, the milk reservoir 20 is detached to pour out the milk through the channel 22. Once the milk reservoir 20 is detached, the tee piece 30 is separate and thus the tee piece 30 and the duckbill valve 50 can be cleaned to ensure sanitary use.

Further, the milk reservoir 20 includes a lid 24 and a reservoir body 25. The lid 24 is ultrasonically welded to the reservoir body 25, such that the lid 24 and the reservoir body 25 are connected to each other in an absolutely sealed manner to avoid milk leakage. The connecting boss 21 is formed on the lid 24. The reservoir body 25 adopts a transparent structure, so that the milk can be observed through the reservoir body 25. The reservoir body 25 is also provided with a capacity scale, so that the user can know the amount of milk sucked out according to the scale.

Figure 10:
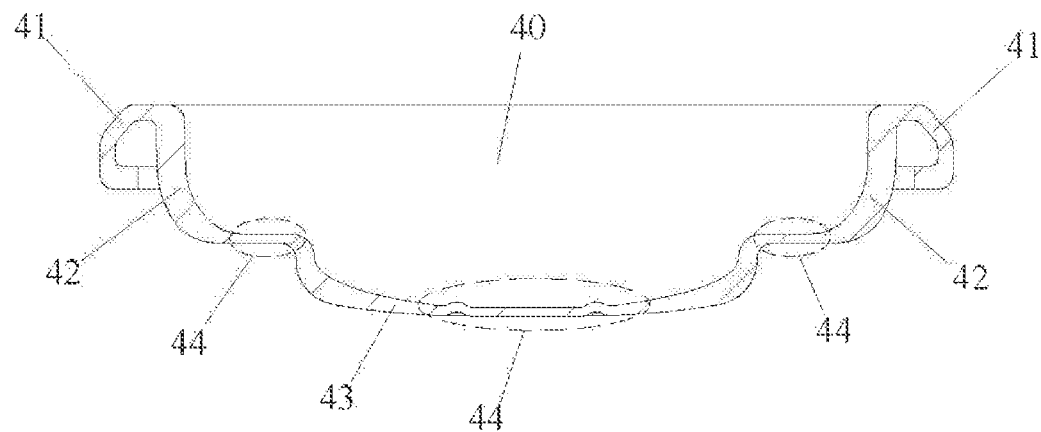
FIG. 10 is a cross-sectional view of the airbag.
Figure 11:
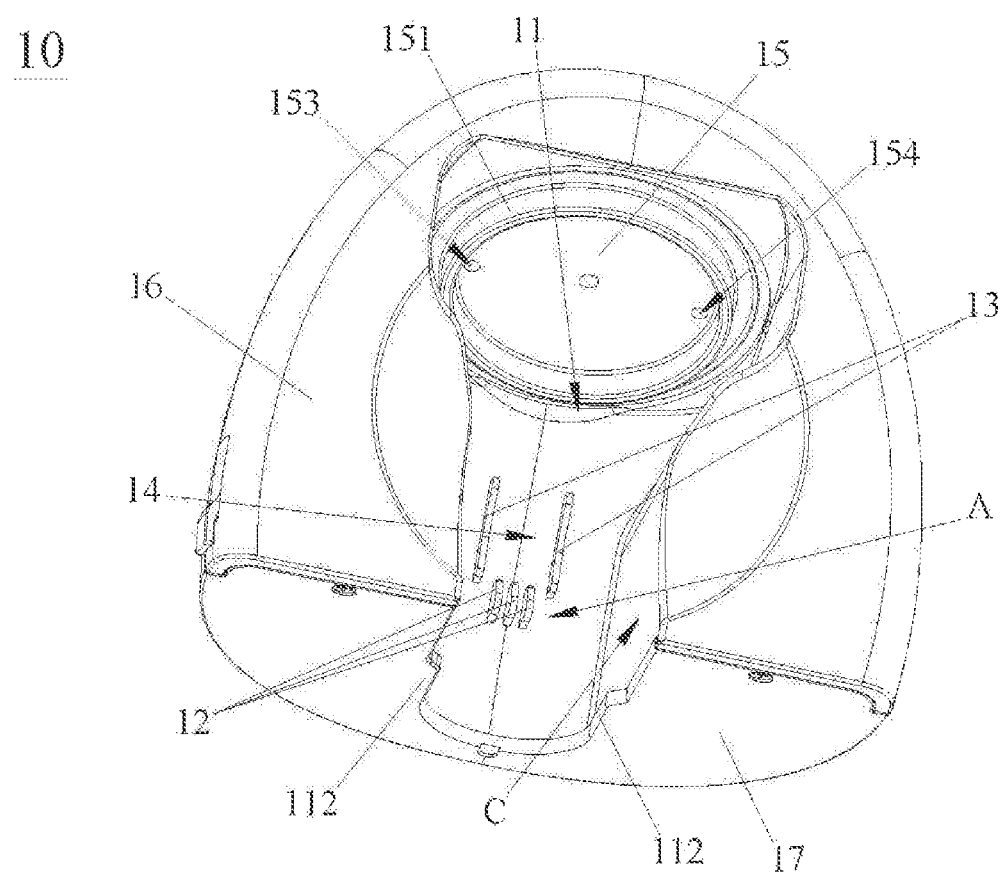
FIG. 11 is a perspective view of the main pump body.

As shown in FIGS. 3 and 10, an end part of the second port D2 of the tee piece 30 is provided with a hook-shaped snap structure 36; the open end of the airbag 40 is formed with a flanging structure 41 arranged outward; and the flanging structure 41 is snap-fitted to the inverted fastening structure 36. In this way, the airbag 40 can be more reliably and stably mounted to the first port of the tee piece 30, and the hook-shaped snap structure 36 is large in volume and can effectively presses the flanging structure 41 against the press cover 15. As shown in FIG. 3, the hook-shaped snap structure 36 and the support ring 151 together enclose a portion of the airbag 40.

As shown in FIG. 10, the airbag 40 includes an annular structure 42 and a deformation structure 43 protruding downward and connected to the annular structure 42. The deformation structure 43 is centered in the annular structure 42. A thin layer structure 44 is arranged at a joint of the annular structure 42 and the deformation structure 43 and at the center of the deformation structure 43. It should be noted that the thin layer structure 44 means that the thin layer structure 44 is relatively thinner than the rest portion of the airbag 40. Thus, when air is pumped out of the compressible air chamber 152, the thin layer structure 44 deforms first and reacts more quickly, and the rest of the structure deforms slowly. When air enters the compressible air chamber 152, other parts of the compressible air chamber 152 provide support for the thin layer structure 44 due to a small amount of deformation, so that the airbag 40 can be restored to its original shape more quickly.

The following is a brief description of a use process of the breast pump 100 of the present invention. Before use, an underwear is put on, the breast pump 100 is put into the underwear, the breast shield structure 31 is placed over a breast, a nipple is extended into the nipple sleeve 311, and the breast pump 100 is adjusted, such that the front end surface of the breast pump 100 is attached to the skin around the breast. Next, the start function mode button is pressed to start the breast pump 100. The air pump 18 pumps out air in the compressible air chamber 152, so that the airbag 40 contracts and a negative pressure is formed in the inner cavity of the tee piece 30 to squeeze out breast milk, and the duckbill valve 50 is closed at this time. Then, the solenoid valve 19 is opened, the ambient air enters the compressible air chamber 152, the airbag 40 is restored to its original shape, the duckbill valve 50 is opened, and the milk flows into the milk reservoir 20. The process is continuously repeated, and thus breast milk can be pumped out.

After breast pumping, the breast pump 100 is removed from the breast. When the tee piece 30 and the milk reservoir 20 are forced in the forward direction of the breast pump 100, the snap-fit structure 23 slides out of engagement with the counter snap-fit structure 112; and after the milk reservoir 20 is removed, the milk in the milk reservoir 20 can be poured out. By detaching the duckbill valve 50 from tee piece 30, and the tee piece 30 and duckbill valve 50 can be cleaned separately to ensure sanitary use. The tee piece 30, the duckbill valve 50 and the milk reservoir 20 can be reassembled before next use.

Figure 2:
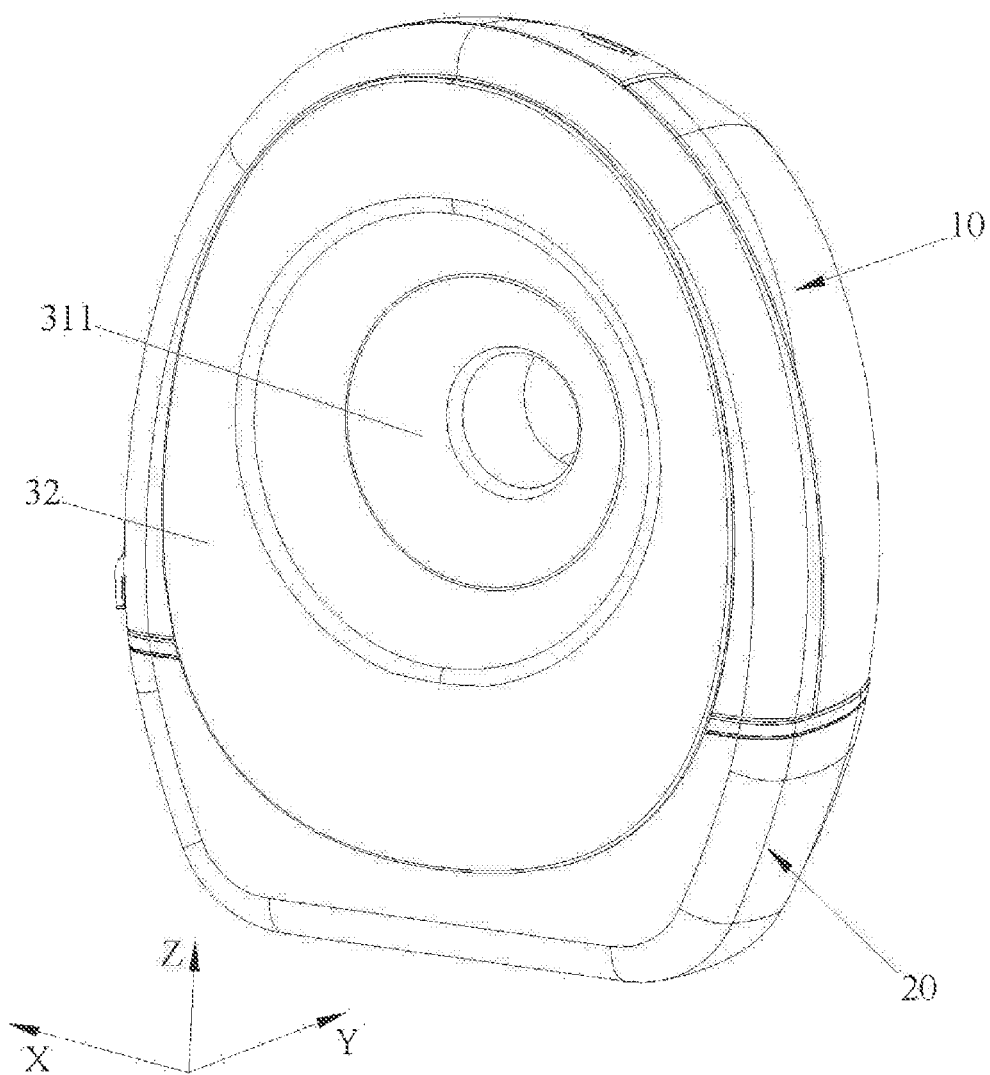
FIG. 2 is a perspective view of the breast pump from another angle.

It should be noted that in FIGS. 1 and 2, the Arrow X indicates a rightward direction, the arrow Y indicates a rearward direction, and the arrow Z indicates an upward direction, but the present invention is not limited thereto.

The above disclosure is only a preferred example of the present invention and cannot be used to limit the scope of the present invention. Therefore, equivalent changes made in accordance with the claims of the present invention fall within the scope of the present invention.

What is claimed is:
1. A hands-free wearable breast pump, comprising:
a main pump body,
a milk reservoir,
a tee piece,
an airbag, and
a duckbill valve, wherein the main pump body is provided with a mounting cavity having an opening in a front end surface of the main pump body; the tee piece comprises a first port, a second port for mounting the airbag and a third port for mounting the duckbill valve; the airbag is mounted to the second port; the duckbill valve is mounted to the third port; the milk reservoir is mounted to the tee piece or the main pump body; the duckbill valve is in fluid communication with the milk reservoir; the main pump body has at least one pushing and positioning structure formed in the mounting cavity; the tee piece is detachably mounted in the mounting cavity and abuts against the at least one pushing and positioning structure; and the tee piece is pushed upward by the at least one pushing and positioning structure to press an open end of the airbag against a side wall of the mounting cavity;
a rear side of the tee piece is formed with a counter pushing and positioning structure;
the mounting cavity is surrounded by a rear side surface opposite the front end surface and a left side surface and a right side surface;
the main pump body is provided with two limiting structures protruding from the rear side surface and arranged at an interval with one on the left side surface and an other on the right side surface; the two limiting structures are arranged above the at least one pushing and positioning structure; the two limiting structures and the at least one pushing and positioning structure define a positioning space; and the counter pushing and positioning structure is arranged in the positioning space;
the two limiting structures are vertically extending tab structures; the two limiting structures are symmetrically arranged opposite each other; the rear side of the tee piece is also formed with an auxiliary positioning structure; the auxiliary positioning structure is located above the counter pushing and positioning structure; the auxiliary positioning structure and the counter pushing and positioning structure are horizontally extending tab structures; the auxiliary positioning structure is arranged in the positioning space; and the rear side of the tee piece is formed with a connecting structure connecting the counter pushing and positioning structure and the auxiliary positioning structure.

2. The hands-free wearable breast pump of claim 1, wherein the first port of the tee piece is integrally formed into a breast shield structure; and the breast shield structure penetrates through the front end surface of the main pump body.

3. The hands-free wearable breast pump of claim 1, wherein the counter pushing and positioning structure and the at least one pushing and positioning structure are arranged to abut against each other; a bottom surface of the counter pushing and positioning structure is a horizontally arranged flat structure; a top portion of the at least one pushing and positioning structure is a horizontal structure; and a front side surface of the at least one pushing and positioning structure is arranged obliquely.

4. The hands-free wearable breast pump of claim 1, wherein the main pump body is provided with a plurality of the at least one pushing and positioning structures protruding from the rear side surface and arranged side by side at intervals.

5. The hands-free wearable breast pump of claim 1, wherein the main pump body comprises a press cover arranged at a top of the mounting cavity; the press cover has a support ring protruding towards the mounting cavity; the open end of the airbag is snap-fitted to the second port of the tee piece; the second port of the tee piece and the press cover together compress the open end of the airbag; the support ring extends into the airbag; the press cover and the airbag define a compressible air chamber of variable volume; and the press cover is provided with an air outlet and an air inlet in fluid communication with the compressible air chamber.

6. The hands-free wearable breast pump of claim 1, wherein a connecting boss protrudes from a top portion of the milk reservoir; the connecting boss is provided with a channel in fluid communication with an inner cavity of the milk reservoir; the duckbill valve extends through the channel; the connecting boss comprises a snap-fit structure; the main pump body comprises a counter snap-fit structure; and the milk reservoir is detachably mounted to the main pump body by snap fit of the snap-fit structure and the counter snap-fit structure.

7. The hands-free wearable breast pump of claim 1, wherein the airbag comprises an annular structure and a deformation structure protruding downward and connected to the annular structure; the deformation structure is centered in the annular structure; and a thin layer structure is arranged at a joint of the annular structure and the deformation structure and/or at a center of the deformation structure.

8. The hands-free wearable breast pump of claim 1, wherein an end part of the second port of the tee piece is provided with a hook-shaped snap structure; the open end of the airbag is formed with a flanging structure arranged outward; and the flanging structure is snap-fitted to the hook-shaped snap structure.

* * * * *